US00PP20764P2

(12) United States Plant Patent
Delabroye

(10) Patent No.: US PP20,764 P2
(45) Date of Patent: Feb. 16, 2010

(54) ***HEUCHERA* PLANT NAMED 'CHRISTA'**

(50) Latin Name: ***Heuchera* hybrid**
Varietal Denomination: Christa

(75) Inventor: Thierry Delabroye, Hantay (FR)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 12/286,640

(22) Filed: Oct. 1, 2008

(51) Int. Cl.
*A01H 5/00* (2006.01)

(52) U.S. Cl. ..... Plt./440

(58) Field of Classification Search ..... Plt./263, Plt./440

See application file for complete search history.

*Primary Examiner*—Susan B McCormick Ewoldt

(57) ABSTRACT

The new hybrid cultivar of *Heuchera villosa* with lightly cupped foliage of reddish-peach, maturing to multi-shaded with greenish bronze to tan, and light pink flowers and improved heat tolerance.

3 Drawing Sheets

Botanical denomination: *Heuchera* hybrid.
Cultivar designation: 'Christa'.

BACKGROUND OF THE INVENTION

The present invention relates to a new and distinct cultivar of Coral Bells in the Saxifragaceae family and given the cultivar name of 'Christa'. *Heuchera* 'Christa' resulted from a cross between *Heuchera* 'Gloire D'Orléans' (not patented) and *Heuchera villosa* 'Caramel'. The new plant was hybridized and selected from among other seedlings growing at a nursery in Hantay, France in the summer of 2005. *Heuchera* 'Christa' has been asexually propagated by division and by careful tissue culture propagation at the same nursery in Hantay, France and Rijswik, Netherlands, respectively, and the resultant propagules have been remained stable and exhibit the same characteristics as the original plant

BRIEF SUMMARY OF THE INVENTION

*Heuchera* 'Christa' differs from its parents as well as all other Coral Bells known to the applicant in the following combined traits:

1. The foliage color of 'Christa' emerges a reddish peach in the spring and develops a greenish bronze in full sun.
2. The flower color is a light pink.
3. The plant is compact and is more heat tolerant than hybrids without *Heuchera villosa* in the lineage.

The nearest comparison varieties are *Heuchera* 'Caramel' U.S. Plant Pat. No. 16,560 and *Heuchera* 'Marmalade' U.S. Plant Pat. No. 15,945. The new plant is smaller in plant habit and in leaf size, has more reddish coloration in the leaf in early spring and is more floriferous, with pink flowers compared to the creamy flowers of 'Caramel'. 'Marmalade' has white flowers and more curled foliage than the new plant. In comparison to the parents, *Heuchera* 'Gloire d'Orleans' has smaller green foliage with a dark spot in the center and pink flowers, while *Heuchera* 'Caramel' has cream flowers with less orange in the foliage.

BRIEF DESCRIPTION OF THE DRAWINGS

The photographs of the new plant demonstrate the overall appearance of the plant including the unique traits. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
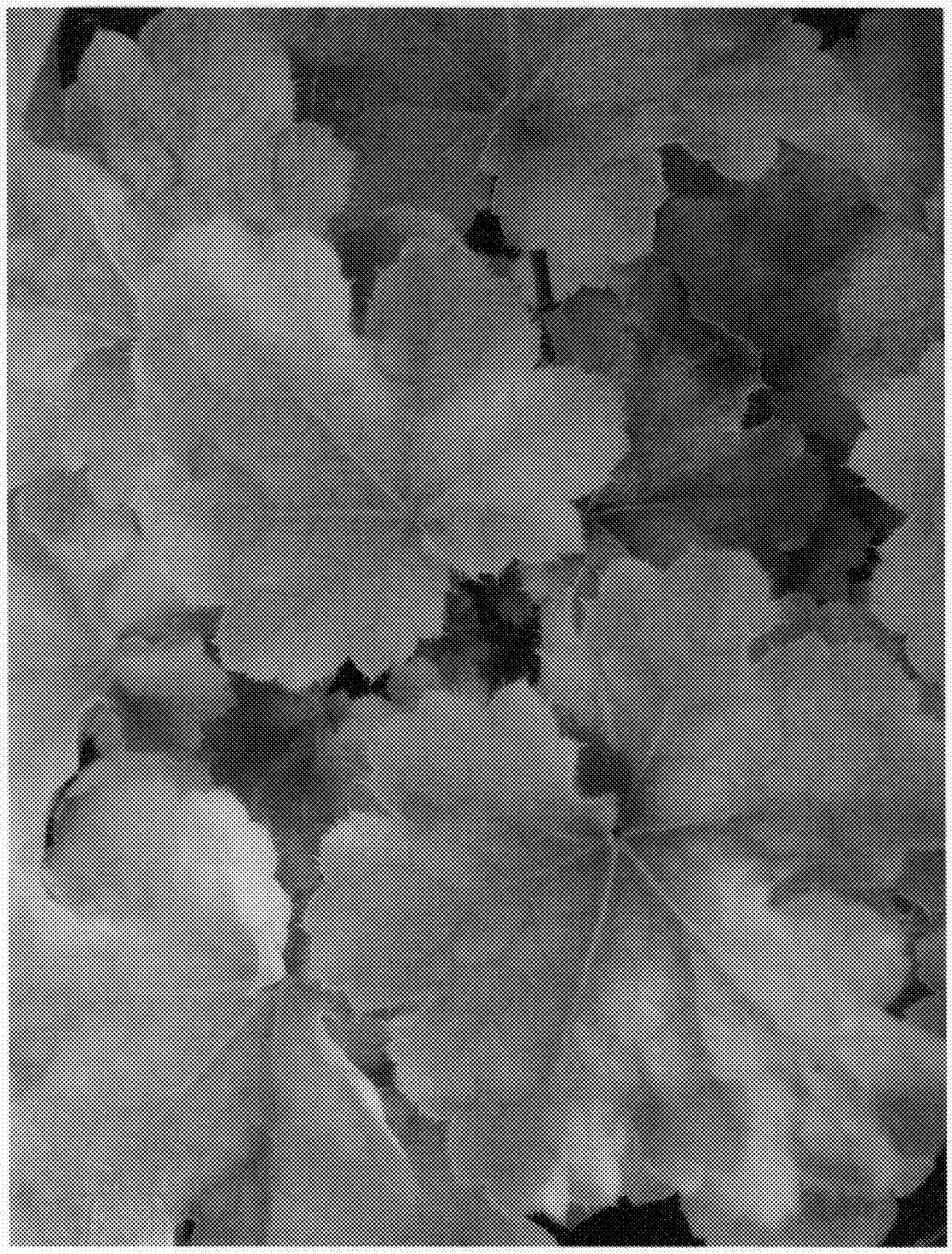
FIG. 1 shows a close-up of the foliage of the new plant in early spring.
Figure 2:
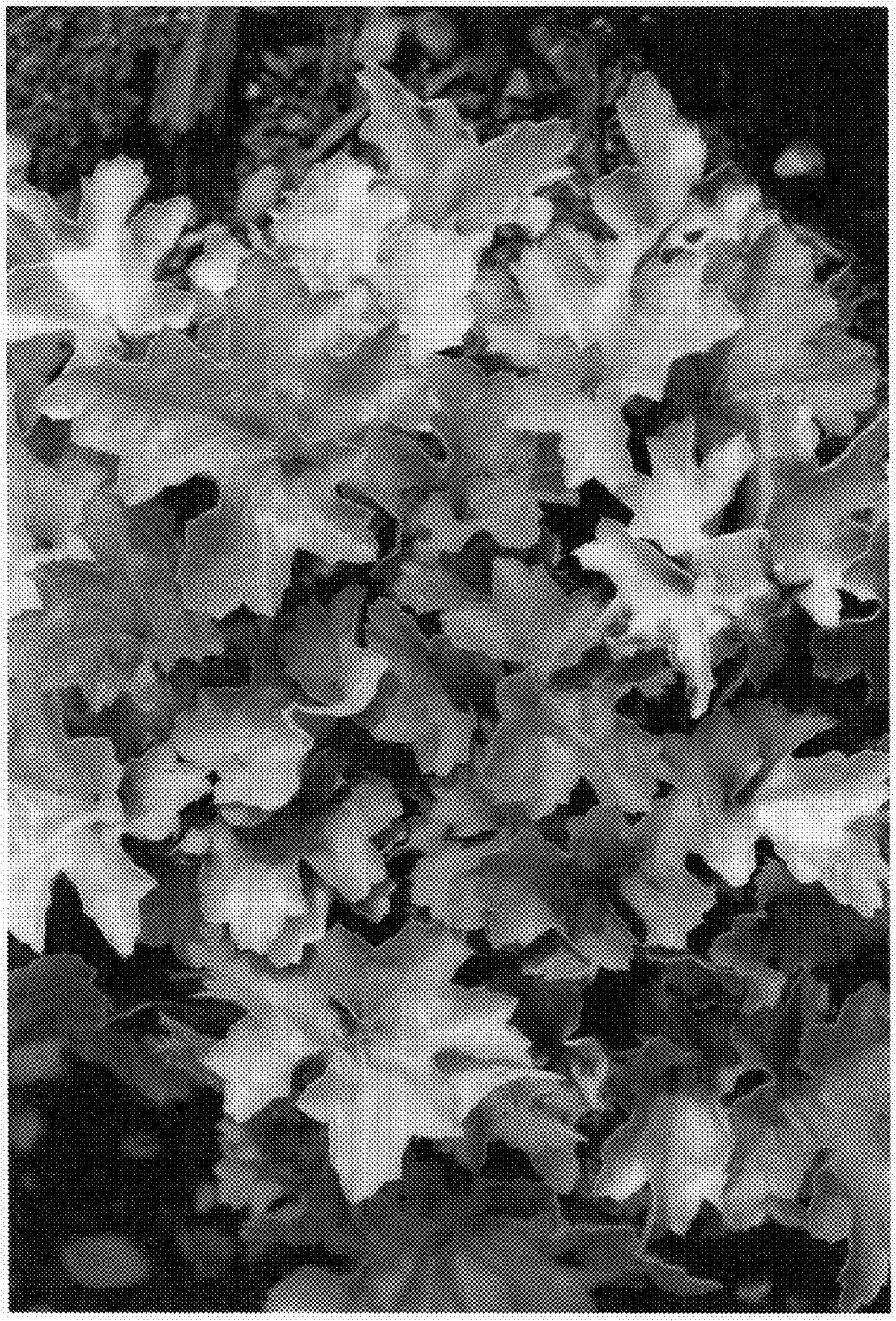
FIG. 2 shows a one-year old plant with fall foliage.
Figure 3:
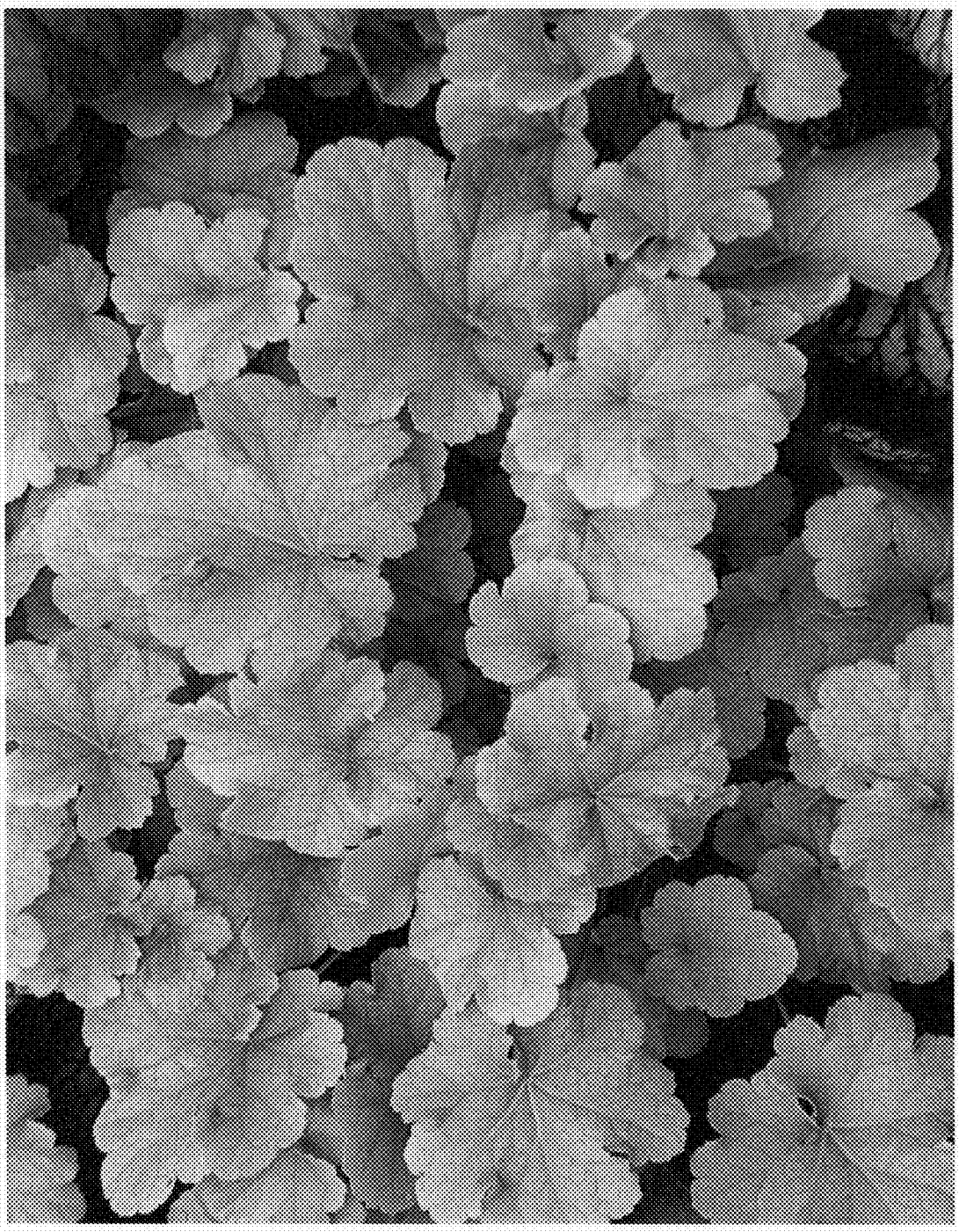
FIG. 3 shows an overhead view of the plant with the various foliage colors in early spring.

The following description is based on a one-year old plant growing in a fill sun trial garden with supplemental water and fertilizer in Zeeland, Mich., U.S.A. The new plant has not been grown under all possible environments and may phenotypically appear different under different conditions such as light, temperatures, fertilizer, and water, without any difference in genotype. The color descriptions used are from the 2001 edition of The Royal Horticultural Society Colour Chart except where common dictionary terms are used.

Parentage: 'Gloire d'Orleans'— female (seed parent); 'Caramel'— male (pollen).

Plant habit: Hardy herbaceous perennial with basal rosette of foliage; mounded foliage about 18 cm tall and 30 cm in diameter.

Roots: Fibrous, finely branched.

Growth rate: Rapid, rooting from cutting in 2 weeks and finishing in three-liter container in about 3 months.

Foliage:

*Leaf.*—Cordate, serrate, palmately lobed, slightly shiny surface above when young in the spring, matte surface below and when mature; blade about 8 cm long and 8 cm wide; undulate to lightly concavely cupped; leaf color is variable, spring young emerging leaves top surface RHS 179B on top and RHS 185B underneath; summer and fall mature leaves in full sun RHS 164D above and RHS 159A with slight violet tinting below, summer and fall mature leaves in some shade can be RHS N170B and closest to RHS 148B with more bronze above and RHS 184A below.

*Leaf margin.*—Serrate and hirtellous between lobe apexes and hirsute at lobe apexes.

*Leaf apex.*—Acute.

*Leaf base.*—Cordate with overlapping lobes.

*Leaf surface.*—Hirtellous both above and below.

*Leaf quantity.*—About 25 per plant.

Veins: Palmate, same color as leaf on top surface; below RHS 186C on emerging foliage, RHS 186B on foliage with shade and RHS 159B.

Petiole: Round, hirsute, about 9 cm long and 2 mm wide; lighter than RHS 183D on older foliage and 185C on emerging foliage.

Inflorescence: In open panicle, about 15 panicles per plant; about 80 flowers per panicle; each panicle flowering starting in late June for about 3 weeks; no fragrance detected.

Peduncle: Round in cross section, hirsute, about 55 cm tall and 3 mm in diameter; RHS 183C.

Pedicel: Round in cross section, hirtellous, about 10 mm long and 1 mm diameter; RHS 183D.

Buds: One day prior to opening—oblong, about 5 mm long and 2 mm diameter, closest to RHS 63B.

Flower: Campanulate, about 7 mm long and 4 mm in diameter at face; individual flowers lasting about 4 days on plant or on cut panicle.

Petals: Five, apex narrowly acute; about 3 mm long and 1.5 mm wide; nearest RHS 73D on both surfaces.

Androecium: Filaments five, thin, white, lighter than RHS 155D; anthers and pollen have not observed.

Gynoecium: Single style with pistil split at tip; 6 mm long; lighter than RHS 192D.

Calyx: Five-lobed, campanulate, acute apex, 3 mm long, fused in the bottom 1 mm; nearest RHS 137D with tinting of violet.

Fruit: Two-beaked capsule, about 6 mm long and 3 mm in diameter at widest portion; RHS 199A.

Seed: Ovoid, less than 1 mm long and wide; black, RHS 202A.

Disease and pest tolerance: The new plant grows best with ample moisture and drainage in either sun or shade. It is more tolerant of hot conditions than typical Coral Bells. Cold hardy from USDA zones 4 to 9. Other resistance and tolerance outside of that normal for *Heuchera* is not known.

I claim:

1. The new and distinct Coral Bells plant named *Heuchera* 'Christa' as herein described and illustrated with young spring foliage of reddish-peach, maturing to multi-shaded foliage with greenish bronze to tan, comprising light pink flowers, with improved heat tolerance.

* * * * *

HEUCHERA PLANT NAMED 'CHRISTA'

HEUCHERA PLANT NAMED 'CHRISTA'

HEUCHERA PLANT NAMED 'CHRISTA'